United States Patent [19]

Hagemann

[11] Patent Number: 5,792,892
[45] Date of Patent: Aug. 11, 1998

[54] PROCESSES FOR PREPARING AROMATIC, BROMINE-CONTAINING COMPOUNDS, NOVEL BROMINE-CONTAINING COMPOUNDS, AND THEIR USE AS INTERMEDIATE PRODUCTS IN THE SYNTHESIS OF ACTIVE AGENTS

[75] Inventor: Hermann Hagemann, Leverkusen, Germany

[73] Assignee: Bayer Aktiengesellschaft, Leverkusen, Germany

[21] Appl. No.: 732,306

[22] PCT Filed: Apr. 18, 1995

[86] PCT No.: PCT/EP95/01439

§ 371 Date: Oct. 22, 1996

§ 102(e) Date: Oct. 22, 1996

[87] PCT Pub. No.: WO95/29886

PCT Pub. Date: Nov. 9, 1995

[30] Foreign Application Priority Data

Apr. 28, 1994 [DE] Germany .......... 44 14 841.0

[51] Int. Cl.$^6$ .......... C07C 19/08; C07C 22/00; C07C 63/04

[52] U.S. Cl. .......... 570/127; 570/144; 562/493

[58] Field of Search .......... 570/127, 144; 562/493

[56] References Cited

U.S. PATENT DOCUMENTS

2,607,802   8/1952   Britton et al. .
5,565,612   10/1996  Pfirmann et al. .......... 570/127 X

FOREIGN PATENT DOCUMENTS

0 024 516 A1   3/1981   European Pat. Off. .
0 431 373 A3   6/1991   European Pat. Off. .
1063077        5/1952   France .
2105250        4/1972   France .

*Primary Examiner*—Paul F. Shaver
*Attorney, Agent, or Firm*—Sprung Kramer Schaefer & Briscoe

[57] ABSTRACT

The present invention relates to processes for the preparation of bromine-containing aromatic compounds, to novel bromine-containing compounds and to their use as intermediates in the synthesis of active substances. Processes according to the invention for the preparation of known and novel bromine-containing compounds are characterized by specific conditions.

10 Claims, No Drawings

PROCESSES FOR PREPARING AROMATIC, BROMINE-CONTAINING COMPOUNDS, NOVEL BROMINE-CONTAINING COMPOUNDS, AND THEIR USE AS INTERMEDIATE PRODUCTS IN THE SYNTHESIS OF ACTIVE AGENTS

The present invention relates to processes for the preparation of bromine-containing aromatic compounds, to novel bromine-containing compounds and to their use as intermediates in the synthesis of active substances. Processes according to the invention for the preparation of known and of novel bromine-containing compounds are characterized by specific conditions.

The process according to the invention is generally suited to the bromination of aromatic systems. Many aromatic systems can only be subjected to electrophilic bromination under relatively drastic conditions. It is in these cases that the process according to the invention is preferably employed. Examples of such cases are aromatic compounds which are already substituted by electronegative groups and are therefore deactivated. One concrete example is nitrobenzene, but novel bromine-containing compounds are also accessible by the process according to the invention.

The term novel bromine-containing aromatic compounds refers both to compounds which contain the bromine in the aromatic ring system and to compounds in which the bromine is part of a trihalogenomethyl substituent on the aromatic ring system. It refers moreover to compounds which contain the bromine both in the aromatic ring system and in the trihalogenomethyl substituent.

The present invention therefore also relates to compounds of the general formula

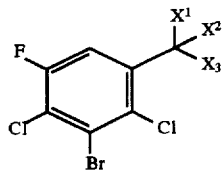

in which $X^1$, $X^2$ and $X^3$ represent halogen, with the proviso that at least one substituent from the group $X^1$, $X^2$ and $X^3$ cannot be fluorine.

3-Bromo-2,4-dichloro-5-fluorobenzotrichloride is preferred.

The aromatic ring system in such bromine-containing aromatic compounds preferably possesses further electron-withdrawing substituents, for example halogens, functional groups at the oxidation state of a carboxylic acid, or nitro groups. Halogen substituents are in particular chlorine and fluorine, and functional groups at the oxidation state of a carboxylic acid are in particular trihalogenomethyl groups, preferably a trichloromethyl group. Concrete examples of the novel bromine-containing aromatic compounds according to the invention are 3-bromo-2,4-dichloro-5-fluorobenzotrichloride (4) and 3-bromo-2,4-dichloro-5-fluorobenzodichloride monobromide (5), which can be used advantageously as intermediates in the synthesis of highly active quinolonecarboxylic acids.

As intermediates for quinolonecarboxylic acids the compounds are used by hydrolysis of the trihalogenomethyl group to give 3-bromo-2,4-dichloro-5-fluorobenzoic acid or by its partial hydrolysis to give the corresponding 3-bromo-2,4-dichloro-5-fluorobenzoyl chloride or bromide.

3-Bromo-2,4-dichloro-5-fluorobenzoic acid and 3-bromo-2,4-dichloro-5-fluorobenzoyl chloride are known as intermediates for highly active quinolonecarboxylic acids and can be prepared, in accordance with DE-A 3 631 906, by nitrating 2,4-dichloro-5-fluorobenzoic acid in position 3, hydrogenating the product to give the amino compound, and introducing bromine by way of a Sandmeyer reaction. The numerous and laborious reaction steps make this route very expensive.

It has now surprisingly been found that 2,4-dichloro-5-fluorobenzotrichloride (1), an industrial intermediate for quinolonecarboxylic acids, can be brominated directly in position 3 under specific conditions with outstanding space-time yield in a process in which, depending on the reaction conditions, the product is, with a substantial degree of uniformity, the novel 3-bromo-2,4-dichloro-5-fluorobenzotrichloride (4), or the analogous dichloromonobromomethyl compound formed by bromine/chlorine exchange in the side chain, as an additional, novel intermediate. Both compounds can be hydrolysed to give the carboxylic acid or, respectively, the carboxylic halide, in analogy to known processes.

2,4-Dichloro-5-fluorobenzyl chloride which is formed during the hydrolysis from any unreacted 2,4-dichloro-5-fluorobenzotrichloride (1) can readily be removed by distillation and is likewise an intermediate for the preparation of quinolonecarboxylic acids.

The process according to the invention is carried out in the presence of Friedel-Crafts catalysts, bromine and chlorine or else substances which give off chlorine, such as sulphuryl chloride. Examples of such catalysts are iron(III) chloride and aluminium chloride, with preference being given to aluminium chloride. In addition the possibility must exist for ClBr to form rapidly during the reaction. A brominating agent which can be employed here, in accordance with the invention, is elemental bromine. For this reaction it is preferred for chlorine to be passed into the reaction mixture, preferably at a temperature of from 20° to 90° C., in the presence of the Friedel-Crafts catalyst, the compound to be brominated and elemental bromine.

The actual ring bromination reagent which will occur in this case is the combination of the compound ClBr (3) and $AlCl_3$: the complex $AlCl_4^{\ominus}Br^{\oplus}$, which is apparently formed much more quickly, or appears in a higher concentration, than the corresponding complex $AlCl_3Br^{\ominus}Br^{\oplus}$ and thus has the outstanding activity according to the invention.

In addition, it is surprising that virtually no chlorination of the aromatic ring system takes place under these reaction conditions if the temperature regime and stoichiometry are appropriate.

Without the introduction of chlorine, the formation of ClBr (3) apparently takes place by Cl/Br exchange in the side chain, as shown by the formation according to the invention of 2,4-dichloro-5-fluorobenzodichloride monobromide (2) and 3-bromo-2,4-dichloro-5-fluorobenzodichloride monobromide (5) in addition to the corresponding 3-bromo-2,4-dichloro-5-fluorobenzotrichloride (4) under these conditions.

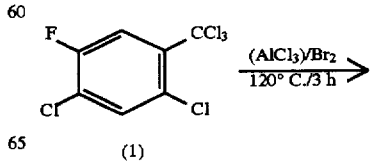

(1)

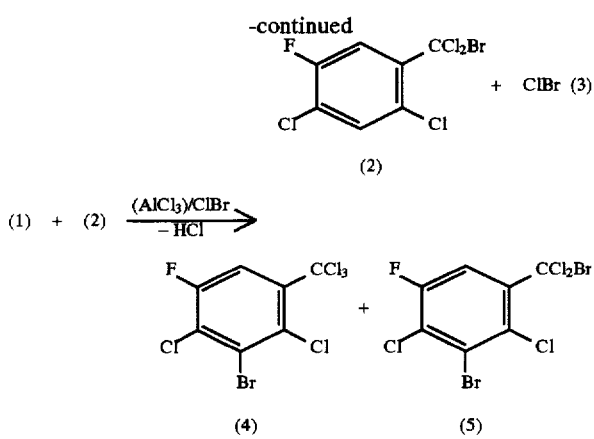

In a preferred embodiment of the process the compound to be brominated is introduced as initial charge together with the Friedel-Crafts catalyst, the mixture is heated to reaction temperature, and preferably preheated bromine, preferably preheated to about 50° C., is introduced continuously from a second reaction vessel, into the reaction vessel containing the compound to be brominated, using a stream of chlorine. Since when chlorine is passed into elemental bromine the compound ClBr (3) with a boiling point of about 5° C. is apparently formed immediately in equilibrium with the two starting elements, apparently ClBr is present in the bromination vessel in so great an excess of chlorine that the surprisingly rapid and selective bromination, as described above, takes place.

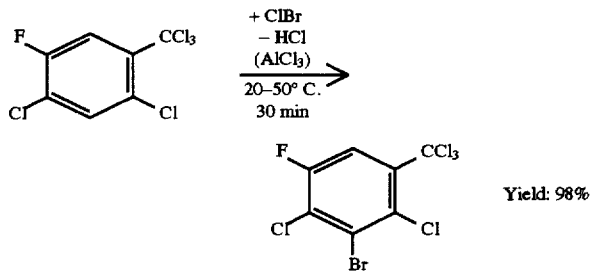

Yield: 98%

The process according to the invention can also be carried out in solvents which are inert under the reaction conditions, the solvents being as known for brominations from the literature. However, the reaction is preferably carried out without solvent.

Bromine is employed in a quantity of 25–200 mol % based on the starting material, preferably 70–150 mol % and particularly preferably 90–120 mol %. Chlorine or a chlorine-donating compound is employed in a quantity which is generally about 10–20 mol % less than the quantity of bromine employed, i.e. about 15–190 mol % based on the compound to be brominated, preferably 60–130 mol % and particularly preferably 80–100 mol %.

The quantity of catalyst is from 0.05 to 10 mol % based on the starting material, preferably from 1 to 8 mol % and particularly preferably 2–4 mol %. Depending on the substituents on the aromatic ring system, the temperature can be varied within broad limits. For the concrete examples mentioned above it is 0°–180° C.

Bromination is preferably carried out at from 10° to 150° C., particularly preferably from 20° to 90° C.

The bromination is generally carried out at atmospheric pressure, although it is also possible to work under pressure, for example at up to 5 bar, and to release—continuously or at intervals—in the ideal case the hydrogen chloride which is formed, which in practice is hydrogen chloride in a mixture with hydrogen bromide.

The reaction time for the bromination depends on the nature and quantity of the catalyst and on the temperature.

In addition, in practice the reaction time is also dependent on the batch size. Under the preferred reaction conditions it is about 30 min for a 70 mmol batch.

If it is desired to isolate the 3-bromo-2,4-dichloro-5-fluorobenzotrichloride in pure form, any excess bromine still present and the catalyst can be separated off after the end of bromination using aqueous sodium thiosulphate solution and the organic phase can be fractionally distilled. However, direct fractional distillation is also possible after the end of bromination.

In cases in which unwanted by-products occur towards the end of the reaction under the conditions of bromination, it is preferred to terminate the reaction before complete conversion.

When the abovementioned concrete example 3-bromo-2,4-dichloro-5-fluorobenzotrichloride is used as an intermediate for quinolonecarboxylic acids by hydrolysis of the trichloromethyl group to give 3-bromo-2,4-dichloro-5-fluorobenzoic acid or by its partial hydrolysis to give corresponding 3-bromo-2,4-dichloro-5-fluorobenzyl chloride, the procedure is generally such that the benzotrichloride (4) is reacted with the appropriate quantity of water or an agent which gives off water, for example formic acid.

The water to be employed for the hydrolysis may also be the dilution water of another substance, for example in the form of non-concentrated sulphuric acid. Water or a water-donating substance is employed, in the case of hydrolysis to the acid chloride, in an essentially equimolar quantity, based on the starting material, for example in a quantity of from 0.8 to 1.2 mol, preferably from 0.9 to 1.1 mol and particularly preferably from 0.95 to 1.05 mol of $H_2O$ per mole of starting material.

The hydrolysis is carried out in the presence or absence of a solvent which is inert with respect to the hydrolysis. Examples of solvents which have proved suitable are chlorobenzene or one of the isomeric dichlorobenzenes. It is preferred to carry out the reaction without solvent. The hydrolysis may be carried out purely by thermal means or in the presence of a catalyst. Such catalysts belong to the group of Lewis and Brönsted acids.

Examples of these are: $FeCl_3$, $ZnCl_2$, $ZrOCl_2$, $H_2SO_4$, $SbCl_3$, $AlCl_3$. The hydrolysis of benzotrichlorides to benzoyl chlorides is known in principle (Ullmanns Encyclopdie der technischen Chemie, [Ullmann's Encyclopaedia of Industrial Chemistry], 4th edition, Volume 8 (1974), p. 373). The addition of one of the catalysts mentioned pertains in particular to the hydrolysis of 3-bromo-2-4-dichloro-5-fluorobenzotrichloride (4) as an isolated intermediate. The hydrolysis is carried out at a temperature of from 20° to 200° C., preferably from 80° to 160° C.

The isolated intermediate or the whole reaction mixture of the bromination is for this purpose introduced as initial charge, and brought to the reaction temperature, whereupon the quantity of water mentioned is metered in. The rate of metered addition of water or of the substance which gives off water depends on the temperature, on the removal of heat (exothermic reaction) and on the removal of gas.

The batch is worked up by fractional distillation.

EXAMPLE 1

20 g (70.7 mmol) of 2,4-dichloro-5-fluorobenzotrichloride and 400 mg of aluminium chloride are introduced as initial charge in a three-necked flask with reflux condenser, stirrer, gas inlet and gas outlet device, and 4.2 ml (81 mmol) of bromine heated to about 50° C. are transported from a second vessel into the three-necked flask over the course of 30 min. using 5 g (70.4 mmol) of chlorine from a cylinder of chlorine. The mixture of 2,4-dichloro-5-fluorobenzotrichloride and aluminium chloride, introduced as initial charge at about 20° C., initially heats up to about 50° C. because of the exothermic reaction and thereafter is maintained at about 30° C. by cooling until the end of the metered addition of $Cl_2$ and $Br_2$, or ClBr.

The reaction solution is stirred for about 30 min, 150 ml of dichloromethane are added, and the excess bromine is extracted by shaking with 10% strength aqueous sodium thiosulphate solution. The organic phase is separated off, dried over sodium sulphate, filtered and concentrated at 50° C. and up to a pressure of 20 mbar. 26.2 g of 3-bromo-2, 4-dichloro-5-fluorobenzotrichloride are obtained having a purity by GC of 95.5%. At a purity of the 2,4-dichloro-5-fluorobenzotrichloride employed of 97.5%, this corresponds to a yield of about 98% (b.p. 115%/0.1 mbar).

EXAMPLE 2

The procedure of Example 1 is repeated, but instead of the aqueous workup the mixture is heated to 140° C. after the end of the bromination reaction and excess bromine is driven off with nitrogen. 0.32 g (3 mol %) of $FeCl_3$ is added, and then 1.26 g (70 mmol) of steam are metered in below the surface of the product to be hydrolysed over the course of about 60 minutes while carrying out thorough mixing at the abovementioned temperature. Reaction is allowed to continue for 30 minutes, and yields 21.5 g of a product which according to GC contains 86.5% 3-bromo-2,4-dichloro-5-fluorobenzoyl chloride and 6.5% starting material. At a purity of the benzotrichloride employed of 95.5%, this corresponds to a yield of 90.7% of theory.

EXAMPLE 3

The procedure of Example 1 is repeated, but the reaction is carried out with 2 mol of 2,4-dichloro-5-fluorobenzotrichloride.

746.4 g of 3-bromo-2,4-dichloro-5-fluorobenzotrichloride are obtained with a purity according to GC of 95%. At a purity of the 2,4-dichloro-5-fluorobenzotrichloride employed of 97.5%, this corresponds to a yield of about 97.5%.

EXAMPLE 4

The procedure of Example 2 is repeated, but the reaction is carried out with 2 mol of 3-bromo-2,4-dichloro-5-fluorobenzotrichloride and with (10 mol %) of $FeCl_3$. The crude product mixture is distilled in vacuo to give 502 g of 3-bromo-2,4-dichloro-5-fluorobenzotrichloride with a purity according to GC of 96.7% (b.p.$_{0.05}$ 82°–85° C.). At a purity of the benzotrichloride employed of 95%, this corresponds to a yield of 83% of theory.

EXAMPLE 5

62 g of 2,4-dichloro-5-fluorobenzotrichloride and 2.4 g of $AlCl_3$ (8 mol %) are introduced as initial charge in a three-necked flask with reflux condenser, stirrer, gas inlet and gas outlet device, and 40.5 g (0.25 mol) of bromine are added at about 20° C. The mixture is heated to about 110° C. From about 80° C. there is evolution of gas, which finishes after 3 hours. The mixture is worked up as in Example 1. 75.4 g of product are obtained having the following composition:

4.8% 2,4-dichloro-5-fluorobenzotrichloride
4.7% 2,4-dichloro-5-fluorobenzodichloride monobromide
37.5% 3-bromo-2,4-dichloro-5-fluorobenzotrichloride
40.2% 3-bromo-2,4-dichloro-5-fluorobenzodichloride monobromide
12.8% other products.

At a purity of the benzotrichloride employed of 95%, this corresponds to a selectivity of 82.8% with respect to the target molecule, 3-bromo-2,4-dichloro-5-fluorobenzoic acid, in Example 6.

EXAMPLE 6

50 g of a mixture of
3.5% 2,4-dichloro-5-fluorobenzodichloride monobromide
2.2% 2,4-dichloro-5-fluorobenzotrichloride
40.2% 2,4-dichloro-5-fluorobenzodichloride monobromide
37.7% 3-bromo-2,4-dichloro-5-fluorobenzotrichloride
and 2.2 g of $FeCl_3$ (10 mol %) are introduced as initial charge in a three-necked flask with stirrer, reflux condenser, dropping funnel and gas outlet device. The mixture is heated to 110° C., and 5 g (0.27 mol) of water are slowly added dropwise to the reaction solution. The acid begins to precipitate with vigorous evolution of gas. Stirring is continued for 1 hour at 110° C., the mixture is cooled, about 100 ml of water are added, the precipitate is filtered off with suction, washed neutral with water and dried at 80° C./20 mbar, and 36.8 g of a product mixture are obtained which contains about 80% 3-bromo-2,4-dichloro-5-fluorobenzoic acid and about 7% 2,4-dichloro-5-fluorobenzoic acid. m.p. 169° to 170° C.

EXAMPLE 7

36 g of the acid mixture from Example 6 and 140 ml of thionyl chloride are introduced as initial charge in a three-necked flask with stirrer, condenser, thermometer and gas outlet device and are slowly heated to reflux. Vigorous evolution of gas begins at about 50° C., and the suspension develops into a clear solution. Reaction is continued for 1 hour at reflux and then the mixture is cooled and distilled to give 30 g of an acid chloride mixture which contains 90.4% 3-bromo-2,4-dichloro-5-fluorobenzoyl chloride and 6.9% 2,4-dichloro-5-fluorobenzoyl chloride. (b.p.$_{0.1}$ 85° to 90° C.)

EXAMPLE 8

600 ml of 1N NaOH are introduced as initial charge in a three-necked flask with stirrer, thermometer and dropping funnel, and 70 g of 3-bromo-2,4-dichloro-5-fluorobenzoyl chloride (crude product from Example 2) are added to the 1N NaOH over the course of 15 minutes at room temperature. Accompanied by a slight exothermic reaction (to 32° C.) the hydrolysis is over after 1 hour. A slight brown precipitate is filtered off and the acid is precipitated with 10% strength HCl. The acid (58 g) is isolated as in Example 6 and converted to the acid chloride in analogy to Example 7. 51 g of 3-bromo-2,4-dichloro-5-fluorobenzoyl chloride are obtained with a purity by GC of 99%. At a purity of the crude product employed of 94%, this corresponds to a yield of 83% of theory (b.p. 85° C./0.1 mbar).

EXAMPLE 9

5 g of 2,4-dichloro-5-fluorobenzoyl chloride and 0.2 g of $AlCl_3$ (4 mol %) are introduced as initial charge in a three-necked flask with stirrer, reflux condenser, gas inlet and gas outlet device, and 4 g of bromine are added at room temperature. The reaction mixture is heated to about 150° C., and 1.5 g of $Cl_2$ are introduced from a cylinder of chlorine. Stirring is continued for about 30 minutes and the reaction solution is worked up as in Example 1. The following were detected by GC/MS:
82% starting material
7.5% 2,3,4-trichloro-5-fluorobenzoyl chloride
8.2% 3-bromo-2,4-dichloro-5-fluorobenzoyl chloride.

EXAMPLES 10 AND 11

If the procedure of Example 9 is repeated but using Fe filings or $AlCl_3$ as catalyst and not using chlorine, no reaction takes place.

EXAMPLE 12

25 g (0.2 mol) of nitrobenzene and 0.5 g of $AlCl_3$ are introduced as initial charge at 80° C. and are brominated over the course of about 2 hours under conditions as in Example 1. 33 g of 3-bromonitrobenzene are obtained. At a conversion of 89% based on nitrobenzene this corresponds to a selectivity of 92% and to a yield of 82%.

EXAMPLE 13

The procedure of Example 1 is repeated, but 10.008 kg (35.42 mol) of 2,4-dichloro-5-fluorobenzotrichloride and 194 g of aluminium chloride together with 5.066 kg of bromine are introduced as initial charge and, beginning at 20° C., 1.863 kg of chlorine are introduced over the course of 6 hours, during which the temperature is maintained at from about 30° to 40° C. by cooling. Excess halogen is driven off with nitrogen, and 12.137 kg of a crude product are obtained which has a purity of 92% in terms of 3-bromo-2,4-dichloro-5-fluorobenzotrichloride, which can be employed directly in the partial hydrolysis described under Example 2 to give the acid chloride.

I claim:

1. Process for the bromination of aromatic compounds, wherein the bromination is carried out in the presence of aluminum chloride and also bromine and chlorine.

2. Process according to claim 1, wherein the compound to be brominated is introduced as initial charge together with the aluminum chloride and the bromine, and the chlorine is metered in.

3. Process according to claim 1, wherein the compound to be brominated is introduced as initial charge together with the aluminum chloride and preheated bromine is transported from a second vessel into the reaction vessel containing the compound to be brominated, using a stream of chlorine.

4. Process according to claim 1, wherein bromine is employed in a quantity of 25-200 mol %, based on the compound to be brominated, and chlorine is employed in a quantity of about 15-190 mol %, based on the compound to be brominated.

5. Process according to claim 1, wherein the aluminum chloride is employed in a quantity of from 0.05 to 10 mol %, based on the compound to be brominated.

6. The compound 3-bromo-2,4-dichloro-5-fluorobenzotrichloride

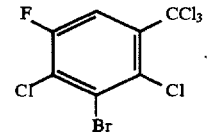

7. Process for the preparation of the compound according to claim 6, wherein a compound of the general formula

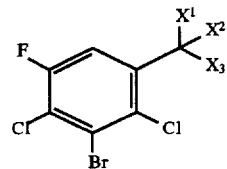

in which $X^1$, $X^2$ and $X^3$ represent three chlorine atoms are brominated in the presence of aluminum chloride and chlorine.

8. Process for the preparation of aromatic bromine-containing compounds by electrophilic bromination, wherein the compound to be brominated is introduced as initial charge with aluminum chloride, and is brominated under conditions in which ClBr or $Cl_4^\ominus Br^\oplus$ or $AlCl_4^\ominus Br^\oplus$ is able to form rapidly.

9. Process according to claim 8, wherein the compounds to be brominated are introduced as initial charge together with the aluminum chloride and preheated bromine is transported from a second vessel into the reaction vessel containing the compound to be brominated, using a stream of chlorine.

10. A method for producing quinolonecarboxylic acids which comprises hydrolyzing the compound of claim 6.

* * * * *

UNITED STATES PATENT AND TRADEMARK OFFICE
CERTIFICATE OF CORRECTION

PATENT NO. : 5,792,892
DATED : August 11, 1998
INVENTOR(S) : Hagemann, Hermann

It is certified that error appears in the above-indentified patent and that said Letters Patent is hereby corrected as shown below:

Col. 1, line 38    Delete formula and substitute

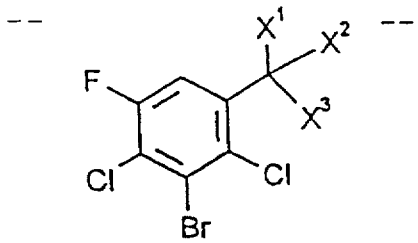

Col. 8, line 25    Delete formula and substitute

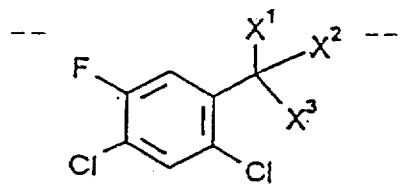

Signed and Sealed this

Twenty-eighth Day of September, 1999

Attest:

Q. TODD DICKINSON

*Attesting Officer*    *Acting Commissioner of Patents and Trademarks*